(12) United States Patent
Zhou et al.

(10) Patent No.: US 8,396,531 B2
(45) Date of Patent: Mar. 12, 2013

(54) SYSTEM AND METHOD FOR QUASI-REAL-TIME VENTRICULAR MEASUREMENTS FROM M-MODE ECHOCARDIOGRAM

(75) Inventors: Shaohua Kevin Zhou, Plainsboro, NJ (US); Feng Guo, Chicago, IL (US); John Jackson, Menlo Park, CA (US); Michael Brendel, Issaquah, WA (US); Dorin Comaniciu, Princeton Junction, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 868 days.

(21) Appl. No.: 12/054,094

(22) Filed: Mar. 24, 2008

(65) Prior Publication Data

US 2008/0281203 A1 Nov. 13, 2008

Related U.S. Application Data

(60) Provisional application No. 60/908,208, filed on Mar. 27, 2007.

(51) Int. Cl.
*A61B 5/00* (2006.01)

(52) U.S. Cl. ........ 600/408; 600/450; 600/463; 382/128; 345/419

(58) Field of Classification Search .................. 600/455, 600/437, 450, 463; 382/128
See application file for complete search history.

(56) References Cited

U.S. PATENT DOCUMENTS

| | | | | |
|---|---|---|---|---|
| 5,701,897 A * | 12/1997 | Sano | ................................ | 600/453 |
| 6,961,454 B2 * | 11/2005 | Jolly | ................................ | 382/131 |
| 7,244,230 B2 * | 7/2007 | Duggirala et al. | ............. | 600/300 |
| 7,400,757 B2 * | 7/2008 | Jolly et al. | ................... | 382/131 |
| 7,450,746 B2 * | 11/2008 | Yang et al. | ..................... | 382/131 |
| 7,507,208 B2 * | 3/2009 | Bennett et al. | ................ | 600/485 |
| 7,547,283 B2 * | 6/2009 | Mourad et al. | ................ | 600/459 |
| 7,558,413 B2 * | 7/2009 | Tu et al. | ........................ | 382/128 |
| 7,583,831 B2 * | 9/2009 | Tu et al. | ........................ | 382/131 |
| 7,593,913 B2 * | 9/2009 | Wang et al. | ...................... | 706/62 |
| 7,648,460 B2 * | 1/2010 | Simopoulos et al. | ......... | 600/437 |
| 7,664,328 B2 * | 2/2010 | Wang et al. | ................... | 382/224 |
| 7,689,283 B1 * | 3/2010 | Schecter | ......................... | 607/18 |
| 7,783,095 B2 * | 8/2010 | Carneiro et al. | ............. | 382/128 |
| 2003/0160786 A1 * | 8/2003 | Johnson | ......................... | 345/419 |
| 2004/0116810 A1 * | 6/2004 | Olstad | ............................ | 600/443 |

(Continued)

OTHER PUBLICATIONS

Jean-Baptiste Fasquel, Vincent Agnus, Luc Soler and Jacques Marescaux, A Hierarchical Topological Knowledge Based Image Segmentationapproach Optimizing the Use of Contextual Regions of Interest: Illustration for Medical Image Analysis, IEEE, 1-4244-0481-9/06.*

(Continued)

*Primary Examiner* — Unsu Jung
*Assistant Examiner* — Serkan Akar

(57) ABSTRACT

A method for measuring ventricular dimensions from M-mode echocardiograms, includes providing a digitized M-mode echocardiogram image, running a plurality of local classifiers, where each local classifier trained to detect a landmark on either an end-diastole (ED) line or an end-systole (ES) line in the image, recording all possible landmarks detected by the classifiers, where a search range in an N-dimensional parameter space defined by the landmarks for each dimension is reduced to a union of subsets, where each dimension of the parameter space corresponds a landmark, for each combination of possible landmarks, checking if an order of the landmarks is consistent with a known ordering of the landmarks, and if the order is consistent, running a global detector on each consistent combination of landmarks to find a landmark combination with a highest detection probability as a confirmed landmark detection, where the landmarks are used for measuring ventricular dimensions.

16 Claims, 6 Drawing Sheets

U.S. PATENT DOCUMENTS

| | | | |
|---|---|---|---|
| 2006/0079773 A1* | 4/2006 | Mourad et al. | 600/438 |
| 2006/0173248 A1* | 8/2006 | Karamanoglu et al. | 600/301 |
| 2007/0016019 A1* | 1/2007 | Salgo | 600/437 |
| 2007/0016034 A1* | 1/2007 | Donaldson | 600/437 |
| 2007/0036414 A1* | 2/2007 | Georgescu et al. | 382/128 |
| 2007/0055153 A1* | 3/2007 | Simopoulos et al. | 600/437 |
| 2007/0081705 A1* | 4/2007 | Carneiro et al. | 382/128 |
| 2007/0130206 A1* | 6/2007 | Zhou et al. | 707/104.1 |
| 2007/0167771 A1* | 7/2007 | Olstad | 600/437 |
| 2008/0009722 A1* | 1/2008 | Simopoulos et al. | 600/437 |
| 2008/0097210 A1* | 4/2008 | Salgo et al. | 600/445 |
| 2008/0240532 A1* | 10/2008 | Carneiro et al. | 382/131 |

OTHER PUBLICATIONS

S. Kevin Zhou1, F. Guo2, J.H. Park1, G. Carneiro1, J. Jackson3,M. Brendel3, C. Simopoulos3, J. Otsuki3, and D. Comaniciul, A probabilistic, hierarchical, and discriminant framework for rapid and accurate detection of deformable anatomic structure, 2007, 978-1-4244-1631-8/07.*

Anders H. Torp, Stein Inge Rabben, Asbjørn Støylen†,Halfdan Ihlen‡, Kai Andersen‡, Lars-A ke Brodin§, Bjørn Olstad, Automatic Detection and Tracking of Left Ventricular Landmarks in Echocardiography, 2004, 0-7803-8412-1/04.*

Tor Arne ig° arda,, H° avard Rueb, Fred Godtliebsenc, Bayesian multiscale analysis for time series data, 2006.07.034.*

Amir A. Amini?, Yasheng Chen?, Jean Sun?, and Vaidy Maniz, Constrained Thin-Plate Spline Reconstruction of 2D Deformations from Tagged MRI, 2006.*

B. Georgescu X. S. Zhou D. Comaniciu A. Gupta, Database-Guided Segmentation of Anatomical Structures with Complex Appearance, 2005.*

Jingdan Zhang‡, Shaohua Kevin Zhou†, Leonard McMillan‡, and Dorin Comaniciu†, Joint Real-time Object Detection and Pose Estimation Using Probabilistic Boosting Network, IEEE, 1-4244-1180-7/07.*

Local discriminative learning for pattern recognition Jing Peng1, Bir Bhanu 1999, Pattern Recognition 34 (2001) 139}150.*

P. Rodriguez V., M. S. Pattichis', M. B. Goens MDz, M-mode Echocardiography Image and Video Segmentation based on AM-FM Demodulation Techniques, Annual international Conference of the IEEE EMBS, 2003.*

Thomas H. Marwick, Rodel L. Leano, Joseph Brown, Jing-Ping Sun, Rainer, Hoffmann, Peter Lysyansky, Michael Becker, and James D. Thomas, Myocardial Strain Measurement With 2-Dimensional Speckle-Tracking Echocardiography: Definition of Normal Range, Dec. 16, 2010, J. Am. Coll. Cardiol. Img. 2009;2;80-84.*

Ömer Nezih Gerek, Member, IEEE, and Dogan Gökhan Ece, Member, IEEE, Power-Quality Event Analysis Using Higher Order Cumulants and Quadratic Classifiers, IEEE Transactions on Power Delivery, vol. 21, No. 2, Apr. 2006.*

Fred L. Bookstein, Principal Warps: Thin-Plate Splines and the Decomposition of Deformations, IEEE Transactions on Pattern Analysis and Machine Intelligence. vol. I I . No. 6. Jun. 1989.*

Gady Agam, Daniel Weiss, Mandar Soman, Probabilistic Brain Lesion Segmentation in DT-MRI, 1-4244-0481—Jun. 6, 2006 IEEE.*

Dorin Comaniciu, Robust Ultrasound Image Analysis Using Learning, 978-1-4244-4126—Jun. 10, 2010 IEEE.*

Hyohoon Choi, Kenneth R. Castlemant, Alan C. Bovikt, Segmentation and Fuzzy-Logic Classification of M-Fish Chromosome, Images, 1-4244-0481—Sep. 6, 2006 IEEE.*

Marina Leitman, MD, Peter Lysyansky, PhD, Stanislav Sidenko, Vladimir Shir, Eli Peleg,MD, Michal Binenbaum, Edo Kaluski, MD, FACC, Ricardo Krakover, MD, and Zvi Vered, MD, Two-dimensional Strain—A Novel Software for Real-time Quantitative Echocardiographic Assessment of Myocardial Function, Copyright 2004 by the American Society of Echocardiograph.*

Ilkay Ulusoy1 and Christopher M. Bishop, Comparison of Generative and Discriminative Techniques for Object Detection and Classification, 2006, Springer.*

Thomas Karavides1,2, K.Y. Esther Leung2, Pavel Paclik3, Emile A. Hendriks1, Johan G. Bosch2, Database Guided Detection of Anatomical Landmark Points in 3D Images of the Heart, 978-1-4244-4126—Jun. 10, 2010 IEEE.*

Tom Brotherton. Tom Pollard. and Pat Simpson, Echocardiogram Structure and Tissue Classification Using Rierarchical Fuzzy Neural Networks, 0-7803-1775-0/94 1994 IEEE.*

Shaohua Kevin Zhou†, Jie Shao‡, Bogdan Georgescu†, and Dorin Comaniciu†, BoostMotion: Boosting a discriminative similarity function for motion estimation, Proceedings of the 2006 IEEE Computer Society Conference on Computer Vision and Pattern Recognition (CVPR'06).*

Zhou et al. Image Based Regression Using Boosting Method, Proceedings of the Tenth IEEE International Conference on Computer Vision (ICCV'05).*

Qazi et al, Automated Heart Wall Motion Abnormality Detection using Sparse Linear Classifiers 2006.*

* cited by examiner

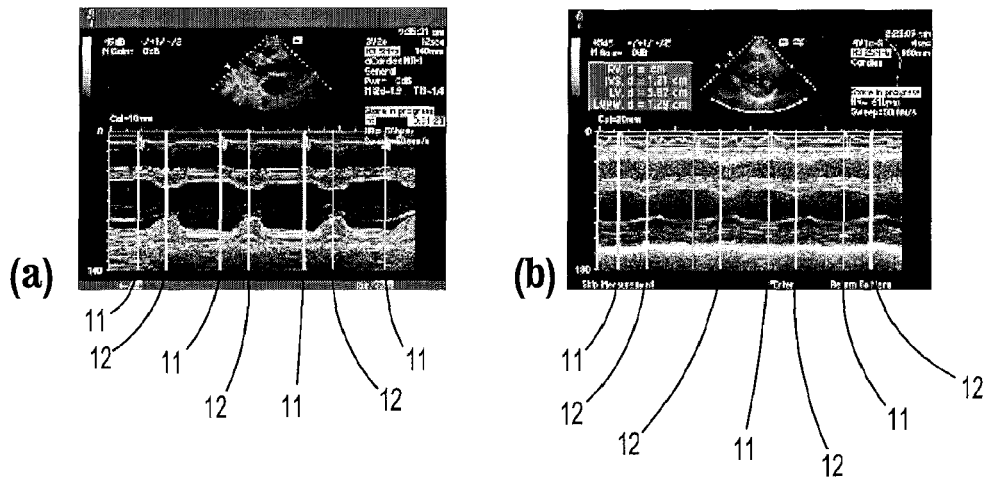

FIG. 1

1. Local detection. For $n = 1, 2, \ldots, N$,
   - Run the local classifier $p_n^L(0|I(y_n))$ and record all possible candidates passing the classifier.
   - (optional) Run a mode seeking procedure to further reduce the number of candidates.
2. Global detection. For each combination of landmarks,
   -Check if the order of the landmarks is consistent.
   -If consistent, invoke the global detector and record the combination with the highest detection probability defined in (4).

| (Unit: cm) | L1d | L2d | L3d | L4d | L5d | L1s | L2s | L3s | L4s | Overall |
|---|---|---|---|---|---|---|---|---|---|---|
| 25%quantile | 0.0000 | 0.0000 | 0.0000 | 0.0000 | 0.0000 | 0.0000 | 0.0000 | 0.0000 | 0.0000 | 0.0000 |
| median | 0.0570 | 0.0326 | 0.0586 | 0.0669 | 0.0586 | 0.0570 | 0.0000 | 0.0000 | 0.0669 | 0.0570 |
| 75%quantile | 0.0669 | 0.0669 | 0.0753 | 0.1256 | 0.0807 | 0.0753 | 0.0669 | 0.0669 | 0.1339 | 0.0753 |
| maximum | 1.6067 | 0.3139 | 0.4100 | 0.6834 | 0.5607 | 1.4310 | 0.5356 | 0.4843 | 0.5607 | 1.6067 |
| mean | 0.0698 | 0.0427 | 0.0531 | 0.0905 | 0.0715 | 0.0579 | 0.0414 | 0.0480 | 0.0878 | 0.0625 |
| std. dev. | 0.1592 | 0.0526 | 0.0593 | 0.1129 | 0.0804 | 0.1166 | 0.0695 | 0.0715 | 0.0912 | 0.0972 |

(b)

| (Unit: cm) | L1d | L2d | L3d | L4d | L5d | L1s | L2s | L3s | L4s | Overall |
|---|---|---|---|---|---|---|---|---|---|---|
| 25%quantile | 0.0669 | 0.0586 | 0.0586 | 0.0753 | 0.0570 | 0.0669 | 0.0570 | 0.0669 | 0.0669 | 0.0628 |
| median | 0.1757 | 0.1256 | 0.0807 | 0.2008 | 0.0807 | 0.1172 | 0.0807 | 0.2278 | 0.1172 | 0.1256 |
| 75%quantile | 0.4017 | 0.2278 | 0.1757 | 0.3347 | 0.1506 | 0.2278 | 0.1614 | 0.4686 | 0.2259 | 0.2422 |
| max | 2.1088 | 4.7532 | 4.6862 | 3.3473 | 2.7444 | 3.5732 | 2.8703 | 3.4708 | 1.9372 | 4.7532 |
| mean | 0.3864 | 0.2959 | 0.2675 | 0.3844 | 0.1841 | 0.2437 | 0.1906 | 0.4055 | 0.1835 | 0.2839 |
| std. dev. | 0.5413 | 0.6303 | 0.7109 | 0.5838 | 0.4155 | 0.4543 | 0.3610 | 0.5703 | 0.2367 | 0.5296 |

(c)

| (Unit: cm) | RVIDd | IVSd | LVIDd | LVPWd | IVSs | LVIDs | LVPWs |
|---|---|---|---|---|---|---|---|
| 25%quantile | 0.0000 | 0.0335 | 0.0359 | 0.0335 | 0.0249 | 0.0000 | 0.0377 |
| median | 0.0359 | 0.0628 | 0.0669 | 0.0669 | 0.0570 | 0.0586 | 0.0628 |
| 75%quantile | 0.0807 | 0.0807 | 0.1172 | 0.0942 | 0.0807 | 0.0807 | 0.1004 |
| maximum | 0.8034 | 0.2422 | 0.3767 | 0.3587 | 0.2152 | 0.4439 | 0.3682 |
| mean | 0.0679 | 0.0640 | 0.0863 | 0.0841 | 0.0596 | 0.0648 | 0.0785 |
| std. dev. | 0.1200 | 0.0497 | 0.0816 | 0.0879 | 0.0532 | 0.0708 | 0.0819 |

(d)

| (Unit: cm) | RVIDd | IVSd | LVIDd | LVPWd | IVSs | LVIDs | LVPWs |
|---|---|---|---|---|---|---|---|
| 25%quantile | 0.0628 | 0.0628 | 0.1076 | 0.0669 | 0.0431 | 0.0807 | 0.0669 |
| median | 0.1614 | 0.1339 | 0.1883 | 0.1464 | 0.1506 | 0.2422 | 0.2278 |
| 75%quantile | 0.3229 | 0.2422 | 0.6054 | 0.3229 | 0.2343 | 0.5378 | 0.5215 |
| maximum | 1.8745 | 3.3473 | 4.4854 | 2.0084 | 1.8745 | 2.2419 | 3.2841 |
| mean | 0.2779 | 0.3459 | 0.5755 | 0.2678 | 0.2850 | 0.4588 | 0.4071 |
| std. dev. | 0.3754 | 0.6089 | 0.9348 | 0.3580 | 0.4551 | 0.5457 | 0.5296 |

FIG. 6

SYSTEM AND METHOD FOR QUASI-REAL-TIME VENTRICULAR MEASUREMENTS FROM M-MODE ECHOCARDIOGRAM

CROSS REFERENCE TO RELATED UNITED STATES APPLICATIONS

This application claims priority from "Accurate and Quasi-real-time Ventricular Measurements from M-mode Echocardiogram", U.S. Provisional Application No. 60/908,208 of Zhou, et al., filed Mar. 27, 2007, the contents of which are herein incorporated by reference in their entirety.

TECHNICAL FIELD

This disclosure is directed to quasi-real time measurements of ventricular dimensions from M-mode echocardiograms.

DISCUSSION OF THE RELATED ART

M-mode echocardiogram is a spatial-temporal image slice of the human heart captured by an ultrasound device. Unlike regular B-mode echo that uses multiple interrogation beams, the M-mode echo uses a single interrogation beam and hence achieves an enhanced temporal and spatial resolution along a single line. It is often used in clinical practice to assess the functionality of anatomic structures inside the heart, such as the left ventricle and aortic root, as its high image quality allows accurate measurement and captures subtle motion.

Ventricular measurements can be derived from the M-mode echo, which can be captured from two windows: the parasternal long axis and the parasternal short axis. FIGS. 1(a)-(b) illustrate ventricular measurements from M-mode echocardiograms for the parasternal long axis window in FIG. 1(a), and for parasternal short axis window in FIG. 1(b). Overlaid on the images are lines 11, 12 indicating the end of diastole (11) and end of systole (12), with expert annotations. In each case, the ultrasound scan line first penetrates the chest wall, then the right ventricle (RV), and finally the left ventricle (LV).

Seven measurements can be obtained from the M-mode echo:

(1) RV internal dimension in diastole (RVIDd);
(2) Interventricular septum thickness in diastole (IVSd);
(3) LV internal dimension in diastole (LVIDd);
(4) LV posterior wall thickness in diastole (LVPWd);
(5) Interventricular septum thickness in systole (IVSs);
(6) LV internal dimension in systole (LVIDs); and
(7) LV posterior wall thickness in systole (LVPWs).

Further, these measurements are derived only on the lines corresponding to the end of diastole (ED) and end of systole (ES), whose positions are either provided beforehand or reliably estimated based on the EKG line. Therefore, the image analysis task is to accurately detect a cohort of landmarks on the given ED and ES lines: five landmarks on an ED line and four landmarks on an ES line. In addition, clinical practices desire computational measurements in quasi-real time, e.g., less than one second.

The N landmark positions can be denoted by $(y_1, y_2, \ldots, y_N)$. For the ED line, N=5, and for the ES line, N=4. Mathematically, one can formulate a high-dimensional search task to tackle the detection:

$$(\hat{y}_1, \hat{y}_2, \ldots, \hat{y}_N) = \underset{(y_1, y_2, \ldots, y_N)}{\mathrm{argmax}}\, p(O\,|\,I(y_1, y_2, \ldots, y_N)), \quad (1)$$

where $I(y_1, y_2, \ldots, y_N)$ is an image patch extracted from the raw image I using the parameter $(y_1, y_2, \ldots, y_N)$ and $p(O|\bullet)$ is the probability of being the target object.

One approach to studying M-mode echo measurements is to detect each landmark independently by training multiple local classifiers, one for each landmark. In other words, this approach assumes that $$p(O\,|\,I(y_1, y_2, \ldots, y_N)) = \prod_{n=1,\ldots,N} p_n^L(O\,|\,I(y_n)), \quad (2)$$

where $I(y_n)$ is a local patch and $p_n^L(O|\bullet)$ is a local classifier. Accordingly the maximization task of EQ. (1) can be reduced to several subtasks:

$$\hat{y}_n = \underset{y_n}{\mathrm{argmax}}\, p_n^L(O\,|\,I(y_n)), n = 1, 2, \ldots, N. \quad (3)$$

Empirical evidence shows a certain effectiveness of the local approach, but it does not meet the accuracy required for clinical practices. It is very fast, though.

Another approach is to detect all landmarks simultaneously by training a global detector $p^G(O|I(y_1, y_2, \ldots, y_N))$. This has a potential of yielding accurate results but renders a search in a high-dimensional parameter space, which obstructs the real time requirement. For example, in order to make the global detector more trainable, one needs to non-rigidly warp the image. Experiments indicate that for an ED line, there are typically over $10^{10}$ image warping possibilities. Performing all these image warping operations can take more than 2 months.

As described earlier, the local approach is fast but inaccurate while the global approach is accurate but slow. One idea is to fuse the local and global approaches, however the challenge is how to combine them in a nontrivial manner such that both speed and accuracy can be guaranteed.

SUMMARY OF THE INVENTION

Exemplary embodiments of the invention as described herein generally include methods and systems for a fast and accurate derivation of ventricular measurements from M-mode echocardiogram that combines local landmark detectors with global template detectors in a probabilistic, hierarchical, and discriminative manner. A learning approach for measuring ventricular dimensions from M-mode echocardiograms in quasi-real time localizes a cohort of landmarks, leading to a high-dimensional searching task. To efficiently explore the high-dimensional parameter space, local landmark detectors and global anatomic structure detectors are fused in a probabilistic, hierarchical, and discriminative manner. Experiments on a set of 89 images record a median absolute error of 0.57 mm in localizing the landmarks while taking about 300 ms to process each image on a standard personal computer with a 3 GHz XEON CPU and 3 GB of memory.

According to an aspect of the invention, there is provided a method for measuring ventricular dimensions from M-mode echocardiograms, including providing a digitized M-mode echocardiogram image comprising a plurality of intensities associated with a 2-dimensional grid, running a plurality of local classifiers, where each local classifier trained to detect a landmark on either an end-diastole (ED) line or an end-systole (ES) line in the image, and recording all possible landmarks detected by the classifiers, where a search range in an N-dimensional parameter space defined by the landmarks for each dimension is reduced into a union of subsets containing the possible landmark detection, where each dimension of the parameter space corresponds to one of the plurality of landmarks, for each combination of possible landmarks, checking if an order of the possible landmarks is consistent with a known ordering of the landmarks, and if the order is consistent, running a global detector on each consistent combination of possible landmarks to find a possible landmark combination with a highest detection probability as a confirmed landmark detection, where the landmarks are used for measuring ventricular dimensions.

According to a further aspect of the invention, there are 5 landmarks on the ED line and 4 landmarks on the ES line.

According to a further aspect of the invention, the method includes smoothing a landmark probability response line output by a local classifier to find all local maxima, ranking the local maxima based on their response magnitudes, and for each local maxima, if a minimum distance of a local maximum with respect to another local maximum in a mode point set is greater than a pre-determined threshold, then the local maximum is added to the mode point set, where the mode point set forms a combination of possible landmarks, and where the mode point set is initialized to local maximum having a highest response from the local classifiers.

According to a further aspect of the invention, the method includes warping locations $\{y_1, \ldots, y_N\}$ of the possible landmarks along a line to coincide with canonical locations $\{z_1, \ldots, z_N\}$ of known landmarks by solving for a function $$f(z) = \sum_{n=1,\ldots,N} c_n \phi(|z - z_n|) + z \cdot d,$$

where $$\phi(r) = r^2 \log(r) \text{ and } \{c_1, c_2, \ldots, c_N, d\}$$

are coefficients, where $y_n = f(z_n)$.

According to a further aspect of the invention, the coefficients $\{c_1, c_2, \ldots, c_N, d\}$ are determined by solving $$\begin{bmatrix} y_1 \\ y_2 \\ \vdots \\ y_N \\ d \end{bmatrix} = \begin{bmatrix} 0 & \phi(|z_1 - z_2|) & \ldots & \phi(|z_1 - z_N|) & z_1 \\ \phi(|z_2 - z_1|) & 0 & \ldots & \phi(|z_2 - z_N|) & z_2 \\ \vdots & \vdots & \vdots & \vdots & \vdots \\ \phi(|z_N - z_1|) & \phi(|z_N - z_2|) & \ldots & 0 & z_N \\ 0 & 0 & \ldots & 0 & 1 \end{bmatrix} \begin{bmatrix} c_1 \\ c_2 \\ \vdots \\ c_N \\ d \end{bmatrix}.$$

According to a further aspect of the invention, each of the local classifiers and the global classifier are binary decision trees trained as probabilistic boosting trees where each tree node is a strong classifier that combines multiple weak classifiers trained on images with pre-identified landmarks.

According to a further aspect of the invention, the weak classifiers are modeled by Haar wavelet features that represent image features.

According to another aspect of the invention, there is provided a program storage device readable by a computer, tangibly embodying a program of instructions executable by the computer to perform the method steps for measuring ventricular dimensions from M-mode echocardiograms.

BRIEF DESCRIPTION OF THE DRAWINGS

FIGS. 1(a)-(b) illustrate ventricular measurements from M-mode echocardiograms, according to an embodiment of the invention.

FIG. 2 presents pseudo-code of a probabilistic, hierarchical, and discriminative algorithm according to an embodiment of the invention.

FIG. 6 is a table of experimental results from pooling together three batches of testing sets, according to an embodiment of the invention.

DETAILED DESCRIPTION OF EXEMPLARY EMBODIMENTS

Figure 3:
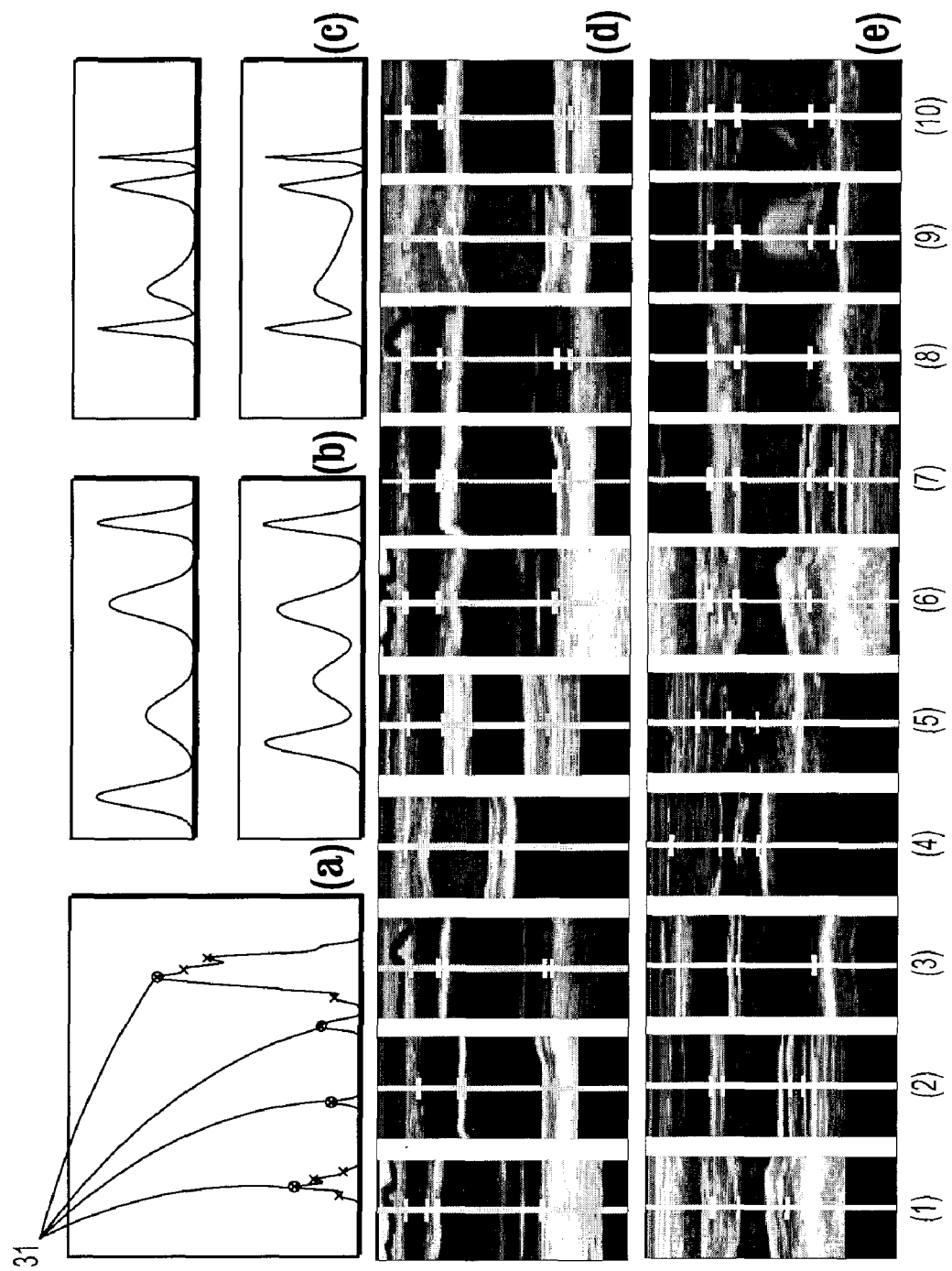
FIG. 3(a) displays a typical probability response map for a landmark and its isolated modes, according to an embodiment of the invention.
FIGS. 3(b)-(c) illustrate a warping process according to an embodiment of the invention.
FIGS. 3(d)-(e) display several pairs of images before and after warping, according to an embodiment of the invention.

Exemplary embodiments of the invention as described herein generally include systems and methods for quasi-real time measurements of ventricular dimensions from M-mode echocardiograms. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Given an image I, the object detection task in an algorithm according to an embodiment of the invention is to seek a configuration $(\hat{y}_1, \hat{y}_2, \ldots, \hat{y}_N)$ that maximizes the overall detection probability defined using a product rule, $$p(O \mid I(y_1, y_2, \ldots, y_N)) = \prod_{n=1,\ldots N} p_n^L(O \mid I(y_n)) \cdot p^G(O \mid I(y_1, y_2, \ldots, y_N)). \quad (4)$$

Using a product rule allows an efficient exploration of the parameter space: if any term in the product is zero (or close to zero), then the overall detection probability is zero (or close to zero). This implies that if one of the classifiers fails to recognize the input as positive, one can simply stop evaluating the remaining classifiers.

Each classifier defines a "feasible" space in which lie the positives. The overall "feasible" space is the intersection of the "feasible" spaces of all classifiers. The goal is to find the maximizing configuration in the overall "feasible" space. FIG. 2 presents pseudo-code of a probabilistic, hierarchical, and discriminative algorithm according to an embodiment of the invention.

Referring now to the figure, a first step of an algorithm according to an embodiment of the invention is local detection, which is equivalent to dimension-wise space pruning. For $n=1, 2, \ldots, N$, the local classifier $p_n^L(O \mid I(y_n))$ is run, and all possible candidates passing the classifier are recorded. By running the local detector on the full search range, those that fail to pass the detector will be filtered out and hence the search space is pruned. In the N-dimensional parameter space, the full search range is reduced for each dimension into a union of subsets that contain positives, e.g., shrinking a large hyper-rectangle into a set of much smaller hyper-rectangles. The candidates close to the ground truth position, or highly confusing spots, are likely to be recorded due to smoothness, which renders a large number of positive candidates. Optionally, a mode selection may be run to decrease the number of candidates, e.g., by representing each small hyper-rectangle by a sparse set of mode points. The mode selection procedure is further described below.

A second step of an algorithm according to an embodiment of the invention is global detection. For each mode point, the algorithm checks if the order of the landmarks is consistent with the known ordering of the landmarks. If yes, then an image warping is performed and the global detector is invoked for verification. The mode point with the highest overall detection probability is used as the final result. The image warping process and the training of the binary detectors for local landmark and global template are described in more detail below.

Mode Selection

Mode selection according to an embodiment of the invention aims to further reduce the search space by finding isolated local maxima. Given a probability response line from a local detector, one first smooths it to find all local maxima. After ranking the local maxima based on their responses, the following operations are performed to find isolated modes.

Let the set of local maxima be $\{y_1, y_2, \ldots, y_M\}$, L the final list of selected modes. The set L is initialized to contain the local maximum that has the highest response in $\{y_1, y_2, \ldots, y_M\}$ and a pre-specified threshold $\lambda$ is defined. For $m=1, 2, \ldots, M$, if the minimum distance $\min_{x \in L} (y_m, x) \geq \lambda$, then add it to L: $L = L \cup \{y_m\}$, otherwise continue. FIG. 3(a) displays a typical probability response map for a landmark and its isolated modes, marked as circles 31.

1-D Warping

Another aspect of an algorithm according to an embodiment of the invention is aligning the global image appearance to place the landmarks in canonical positions. Note that here only 1-D warping is necessary since the x-coordinate is known. Assuming that in the query image, the landmarks are located at $\{y_1, y_2, \ldots, y_N\}$, while in the canonical template, the N landmarks should be positioned at $\{z_1, z_2, \ldots, z_N\}$. One seeks a warping function (or interpolator) $y=f(z)$ that satisfies $y_n=f(z_n)$. FIGS. 3(b)-(c) illustrate a warping process according to an embodiment of the invention. FIG. 3(b) depicts two synthetic signals with the peaks located at different positions before warping, and FIG. 3(c) depicts the peaks of the two signals roughly aligned after warping.

The 2-D thin-plate spline (TPS) warping is widely used for image warping. According to an embodiment of the invention, its 1-D counterpart is used:

$$f(z) = \sum_{n=1,\ldots,N} c_n \phi(|z - z_n|) + z \cdot d, \quad (5)$$

where $\phi(r) = r^2 \log(r)$ is the TPS function and the coefficients $\{c_1, c_2, \ldots, c_N, d\}$ are determined as below. FIGS. 3(d)-(e) display several pairs of images before and after warping. In particular, the row of FIG. 3(d) depicts the ED line and the row of FIG. 3(e) depicts the ES line, and for each, the left five image examples, columns (1) to (5), are before warping and the right five examples, columns (6) to (10), are after warping. Note the variations in the landmark positions and the image intensities.

To determine the coefficients, the conditions $\{y_n = f(z_n), n=1, 2, \ldots, N\}$ are expressed in matrix form:

$$\begin{bmatrix} y_1 \\ y_2 \\ \vdots \\ y_N \\ d \end{bmatrix} = \begin{bmatrix} 0 & \phi(|z_1 - z_2|) & \ldots & \phi(|z_1 - z_N|) & z_1 \\ \phi(|z_2 - z_1|) & 0 & \ldots & \phi(|z_2 - z_N|) & z_2 \\ \vdots & \vdots & \vdots & \vdots & \vdots \\ \phi(|z_N - z_1|) & \phi(|z_N - z_2|) & \ldots & 0 & z_N \\ 0 & 0 & \ldots & 0 & 1 \end{bmatrix} \begin{bmatrix} c_1 \\ c_2 \\ \vdots \\ c_N \\ d \end{bmatrix}. \quad (6)$$

Solving the above linear system yields a unique solution $\{c_1, c_2, \ldots, c_N, d\}$, which stays fixed and is hence pre-computable. Another technique to accelerate evaluating EQ. (5) is to pre-compute a table of values $\phi(r)$ for all possible integers r within a proper range.

Discriminative Learning Via Boosting

According to an embodiment of the invention, a classifier used for measuring ventricular dimensions is derived from the probabilistic boosting tree classifier (PBT), described in Z. Tu., "Probabilistic boosting-tree: learning discriminative models for classification, recognition, and clustering", *International Conference on Computer Vision*, Vol. 2, pp. 1589-1596, 2005, the contents of which are herein incorporated by reference in their entirety. The PBT classifier is a boosting classifier, where the strong classifiers are represented by the nodes of a binary tree. The PBT can cluster data automatically, allowing for a binary classification of data sets presenting multi-modal distributions. Another property of the PBT classifier is that after training, the posterior probability can be used as a threshold to balance between precision and recall.

The PBT trains a binary decision tree, where each node of the tree is a strong classifier that combines multiple weak classifiers via a discriminative boosting procedure. Training the PBT involves a recursive construction of a binary tree, where each of the nodes represents a strong classifier. Each node can be trained with an AdaBoost algorithm, which automatically trains a strong classifier by combining a set of weak classifiers $$H(S) = \sum_{t=1}^{T} \omega_t h_t(S),$$

where S is an image region, $h_t(S)$ is the response of a weak classifier, and $\omega_t$ is the weight associated with each weak classifier. By minimizing the probability of error, the AdaBoost classifier automatically selects the weak classifiers and their respective weights. The probabilities computed by each strong classifier are then denoted as follows:

$$q(+1 \mid S) = \frac{\exp(2H(S))}{1 + \exp(2H(S))} \text{ and } q(-1 \mid S) = \frac{\exp(-2H(S))}{1 + \exp(-2H(S))} \quad (7)$$

Figure 7:
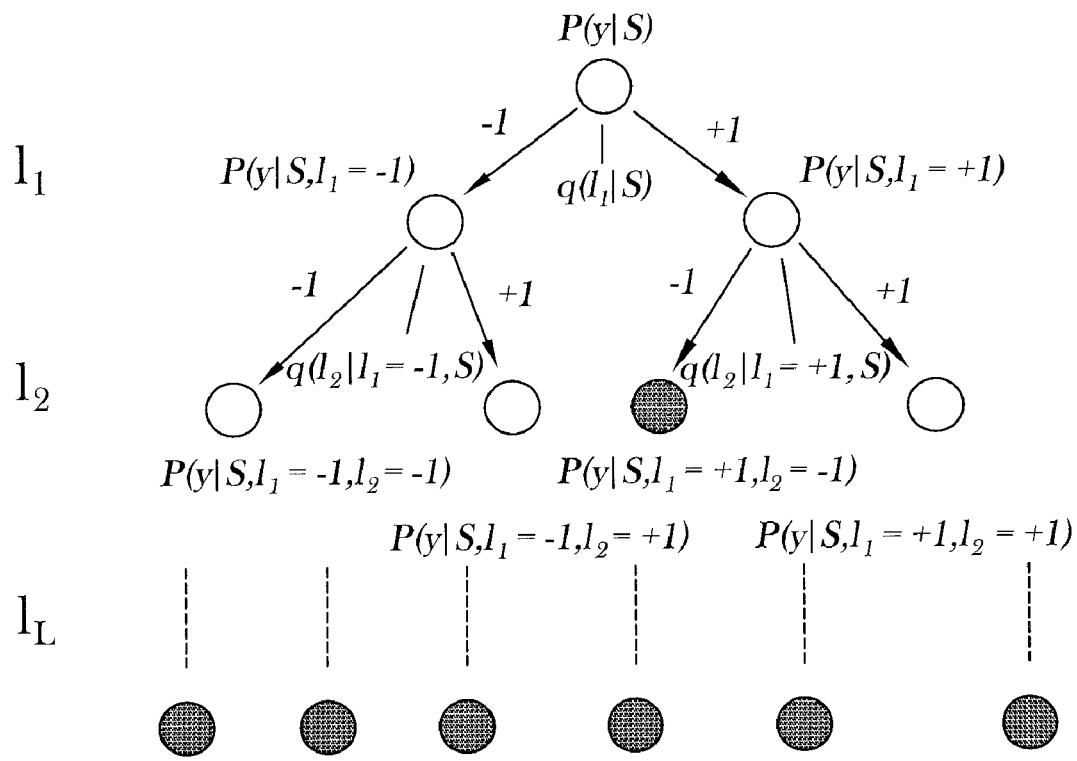
FIG. 7 depicts an exemplary, non-limiting PBT binary tree, according to an embodiment of the invention.

The posterior probability that a region S is foreground (y=+1), or background (y=−1) is computed as:

$$P(y \mid S) = \sum_{l_1, l_2, \ldots, l_n} P(y \mid l_n, \ldots, l_1, S) \ldots q(l_2 \mid l_1, S) q(l_1 \mid S) \quad (8)$$

where n is the total number of nodes of the tree, and $l \in \{-1,+1\}$. An exemplary, non-limiting PBT binary tree is shown in FIG. 7. The dark nodes are the leaf nodes. Each level of the tree corresponds to an augmented variable. Each tree node is a strong classifier. The goal of the learning algorithm is to learn the posterior distribution $p(y|S)$. Each tree level $l_i$ is an augmented variable:

$$\tilde{p}(y \mid S)) = \sum_{l_1} \tilde{p}(y \mid l_1, S) q(l_1 \mid S)$$

$$= \sum_{l_1, l_2} \tilde{p}(y \mid l_2, l_1, S) q(l_2 \mid l_1, S) q(l_1 \mid S)$$

$$= \sum_{l_1, \ldots, l_n} \tilde{p}(y \mid l_n, \ldots, l_1, S) \ldots q(l_2 \mid l_1, x) q(l_1 \mid S).$$

At a tree node, if the exact model can be learned, then $$P(y \mid l_n, \ldots, l_1, S) = \sum_{l_{i+1}} \delta(y = l_{i+1}) q(l_{i+1} \mid l_i, \ldots, l_1, S)$$

where $$\delta(x) = \begin{cases} 1, & \text{if } x = \text{true}, \\ 0, & \text{otherwise.} \end{cases}$$

This means the model $q(l_{i+1} \mid l_i, \ldots, l_1, S)$ perfectly predicts the y and the tree can stop expanding. The augmented variables $l_i$ gradually decouples y from x to make a better prediction. Note that the value $q(l_{i+1} \mid l_i, \ldots, l_1, S)$ is obtained by computing the value of $q(l_{i+1} \mid S)$ at a PBT node reached following the path $l_1 \rightarrow l_2 \rightarrow, \ldots, l_i$, with $l_i$ representing the root node and $l \in \{-1,+1\}$.

Figure 8:
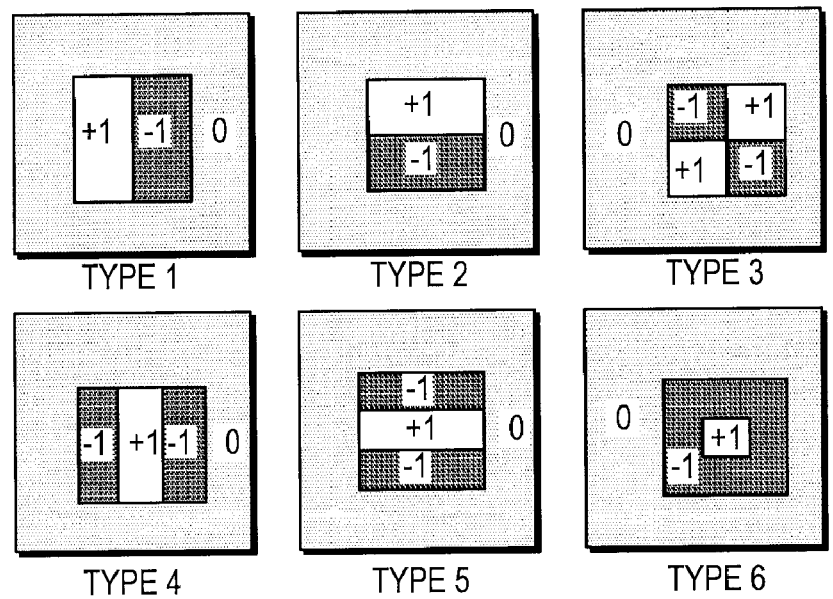
FIG. 8 illustrates some exemplary, non-limiting feature types used in an embodiment of the invention.

The appearance of the image region can be represented with features derived from Haar wavelet, which have the following properties: (1) good modeling power for the different types of visual patterns, such as pedestrians, faces, and left ventricles in ultrasound images; and (2) computation efficiency with the use of integral images. FIG. 8 illustrates some exemplary, non-limiting feature types used in an embodiment of the invention, where each feature is denoted by the following feature vector:

$$\theta_f = [t, x_f, x_f, d_x, d_y, s],$$

where $t \in \{1, \ldots, 6\}$ denotes the feature type, $(x_f, y_f)$ is the top-left coordinate of the feature location, $d_x$ and $d_y$ are the length and width of the spatial support of the feature and $s \in \{+1,-1\}$ represents the two versions of each feature with its original or inverted signs. Note that the feature has the same orientation α as the image region.

The output value of each feature is the difference between the image pixels lying in the white section, represented by +1 in FIG. 8, and the image pixels in the black section, represented by −1 in FIG. 8. The gray regions in FIG. 8 represent the foreground region S. The feature value can be efficiently computed using integral images. An integral image can be computed as follows:

$$T(x, y) = \sum_{i=0}^{x} \sum_{j=0}^{y} I(x, y), \quad (3)$$

where T: $R^{N \times M} \rightarrow R$ denotes the integral image. Then the feature value is computed efficiently through a small number of additions and subtractions.

Experimental Results

An experiment to test a learning approach for measuring ventricular dimensions from M-mode echocardiograms in quasi-real time according to an embodiment of the invention used a library of 89 M-mode images that were annotated by an experienced sonographer. Depending on heart rate and temporal sampling rate, each image contains 1-8 cardiac cycles, with each cardiac cycle contributing a pair of ED/ES lines, although some might have missing ED or ES lines. In total, there are 284 ED lines and 278 ES lines in the database. 70 images were randomly selected for training and the remaining 19 for testing and this random selection was repeated three times for the cross validation purpose.

Figure 4:
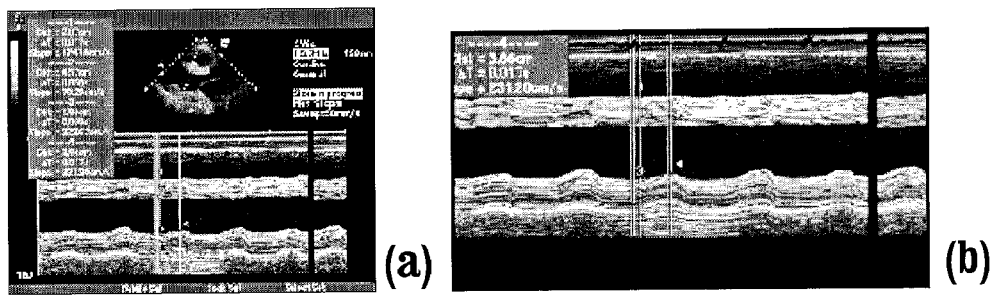
FIGS. 4(a)-(b) show an example of size normalization, according to an embodiment of the invention.

Since the heart rate and the temporal sampling rate are known, the size of each image was normalized in such a way that each cardiac rate spans about the same size (about 125 pixels) in the x-direction. The y-direction was normalized such that each pixel corresponds to about 0.5 mm in depth, and 400 pixels were kept to cover a range from about 0 to 20 cm. After normalization, the images were padded about 5 pixels in each direction for searching convenience and a color detector was used to remove the EKG signal line. FIGS. 4(a)-(b) shows an example of size normalization, with FIG. 4(a) being the original image, and FIG. 4(b) being an M-mode image after size normalization.

The prior ranges for landmarks on the normalized domain are empirically determined based on the database. To train the local classifier, image patches of size 51×51 were cropped around the ground truth positions, with a ±1 perturbation, as positives and those regions 5 pixels away but within the search range were taken as negatives. After training, the PBTs for landmarks had about 400 weak classifiers. To train the global detector, all landmarks were again perturbed around the ground truth positions and warped into canonical positions in the template of size 75×51 to generate positives. Negatives were similarly generated by forcing at least one landmark about 5 pixels away from the true positions. The PBTs for global templates include about 1000 weak classifiers.

During detection, a maximum of five top modes were kept for each landmark, resulting in on the average about 1000 image warpings per ED/ES line. Speed wise, it takes about 300 ms to process one image containing about 3 cardiac cycles on a standard PC with 3 GHz Xeon CPU and 3 GB memory: about 100 ms on size normalization, 150 ms for local detection, and 50 ms for global detection. If an image contains multiple cardiac cycles, the measurement median was computed from multiple cycles as the final output.

Figure 5:
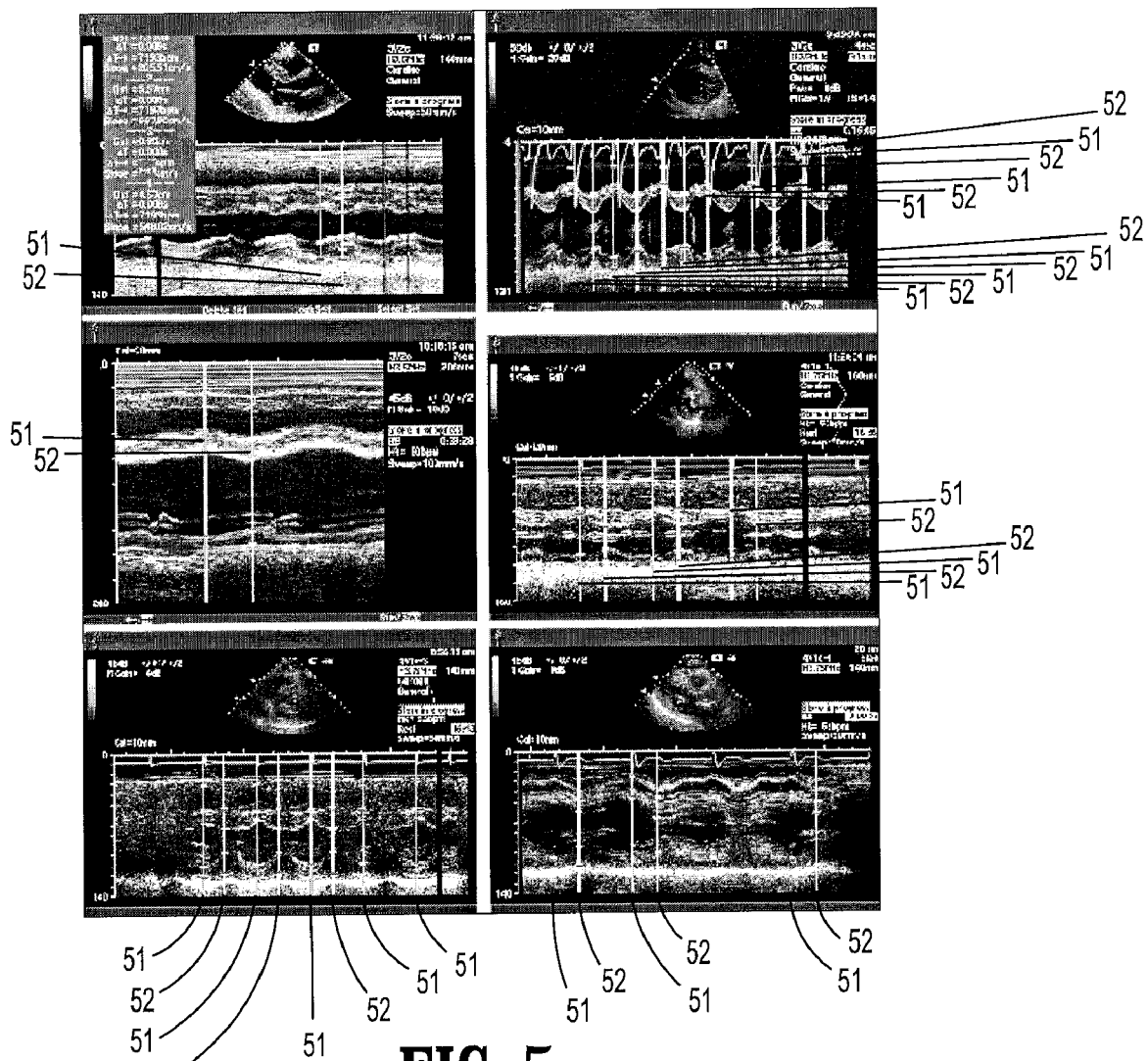
FIG. 5 shows the detection results, according to an embodiment of the invention.

The absolute errors in landmark localization and measurements were used to calibrate the performance. Table 1(a)-(b), shown in FIG. 6, tallies the experimental results by pooling together three batches of testing sets. For comparison, a local approach was also implemented, which finds the landmarks independently. Table 1(a) presents the testing errors in landmark localization obtained by an algorithm according to an embodiment of the invention and Table 1(b) by a local approach. Table 1(c) presents the testing error in measurements obtained by an algorithm according to an embodiment of the invention, and Table 1(d) by a local approach. Collectively, there are 185 ED lines and 187 ES lines for testing, and 57 data points per measurement. From Table 1, it is observed that (1) all results for different landmarks are quite consistent except a few outliers, (2) the overall median absolute error in landmark localization is 0.0570 cm and the mean error is 0.0625 cm, amounting to a subpixel error in the original image, and (3) as the median is used for the measurements, there are fewer outliers. FIG. 5 shows the detection results. The lines 51 correspond to ED and the lines 52 to ES. The detected landmarks are the cross bars on the ED lines and the ES lines, with the ground truth landmarks. The detected landmarks are very close to the true ones despite variances in landmark positions and image intensities. The results for the local approach are worse than those in Table 1(a)-(b). However, in terms of computation, it is faster than an algorithm according to an embodiment of the invention, taking about 50 ms less to process one image.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 9:
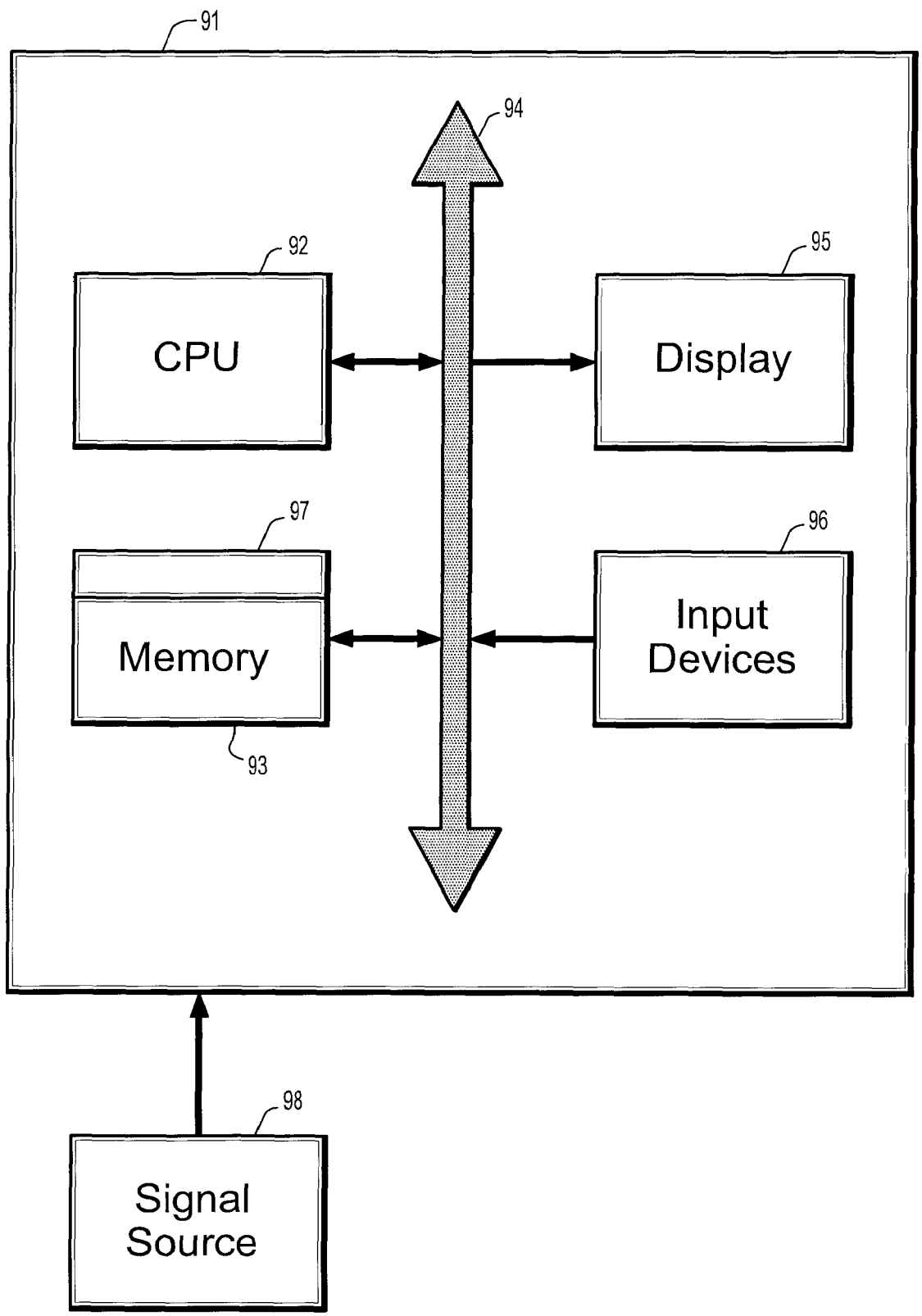
FIG. 9 is a block diagram of an exemplary computer system for implementing a method for quasi-real time measurements of ventricular dimensions from M-mode echocardiograms, according to an embodiment of the invention.

FIG. 9 is a block diagram of an exemplary computer system for implementing a method for quasi-real time measurements of ventricular dimensions from M-mode echocardiograms according to an embodiment of the invention. Referring now to FIG. 9, a computer system 91 for implementing the present invention can comprise, inter alia, a central processing unit (CPU) 92, a memory 93 and an input/output (I/O) interface 94. The computer system 91 is generally coupled through the I/O interface 94 to a display 95 and various input devices 96 such as a mouse and a keyboard. The support circuits can include circuits such as cache, power supplies, clock circuits, and a communication bus. The memory 93 can include random access memory (RAM), read only memory (ROM), disk drive, tape drive, etc., or a combinations thereof. The present invention can be implemented as a routine 97 that is stored in memory 93 and executed by the CPU 92 to process the signal from the signal source 98. As such, the computer system 91 is a general purpose computer system that becomes a specific purpose computer system when executing the routine 97 of the present invention.

The computer system 91 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer implemented method for measuring ventricular dimensions from M-mode echocardiograms, the method performed by the computer comprising the steps of:
    providing to a computer a digitized M-mode echocardiogram image comprising a plurality of intensities associated with a 2-dimensional grid;
    running a plurality of local classifiers, wherein each local classifier trained to detect a landmark on either an end-diastole (ED) line or an end-systole (ES) line in said image, and recording all possible landmarks detected by said classifiers, wherein a search range in an N-dimensional parameter space defined by said landmarks for each dimension is reduced into a union of subsets containing said possible landmark detection, wherein each dimension of said parameter space corresponds to one of the plurality of landmarks;
    for each combination of possible landmarks, checking if an order of the possible landmarks is consistent with a known ordering of said landmarks; and
    if said order is consistent, running a global detector on each consistent combination of possible landmarks to find a possible landmark combination with a highest detection probability as a confirmed landmark detection, wherein said landmarks are used for measuring ventricular dimensions.

2. The method of claim 1, wherein there are 5 landmarks on the ED line and 4 landmarks on the ES line.

3. The method of claim 1, further comprising:
    smoothing a landmark probability response line output by a local classifier to find all local maxima;
    ranking the local maxima based on their response magnitudes; and for each local maxima, if a minimum distance of a local maximum with respect to another local maximum in a mode point set is greater than a pre-determined threshold, then said local maximum is added to the mode point set, wherein said mode point set forms a combination of possible landmarks, and wherein said mode point set is initialized to local maximum having a highest response from said local classifiers.

4. The method of claim 1, further comprising:
warping locations $\{y_1, \ldots, y_N\}$ of said possible landmarks along a line to coincide with canonical locations $\{z_1, \ldots, z_N\}$ of known landmarks by solving for a function $$f(z) = \sum_{n=1,\ldots,N} c_n \phi(|z-z_n|) + z \cdot d,$$

where $\phi(r)=r^2 \log(r)$ and $\{c_1, c_2, \ldots, c_N, d\}$ are coefficients, wherein $y_n=f(z_n)$.

5. The method of claim 4, wherein the coefficients $\{c_1, c_2, \ldots, c_N, d\}$ are determined by solving $$\begin{bmatrix} y_1 \\ y_2 \\ \vdots \\ y_N \\ d \end{bmatrix} = \begin{bmatrix} 0 & \phi(|z_1-z_2|) & \ldots & \phi(|z_1-z_N|) & z_1 \\ \phi(|z_2-z_1|) & 0 & \ldots & \phi(|z_2-z_N|) & z_2 \\ \vdots & \vdots & \vdots & \vdots & \vdots \\ \phi(|z_N-z_1|) & \phi(|z_N-z_2|) & \ldots & 0 & z_N \\ 0 & 0 & \ldots & 0 & 1 \end{bmatrix} \begin{bmatrix} c_1 \\ c_2 \\ \vdots \\ c_N \\ d \end{bmatrix}.$$

6. The method of claim 1, wherein each of said local classifiers and said global classifier are binary decision trees trained as probabilistic boosting trees wherein each tree node is a strong classifier that combines multiple weak classifiers trained on images with pre-identified landmarks.

7. The method of claim 6, wherein said weak classifiers are modeled by Haar wavelet features that represent image features.

8. A computer implemented method for measuring ventricular dimensions from M-mode echocardiograms, the method performed by the computer comprising the steps of:
providing to a computer a digitized M-mode echocardiogram image comprising a plurality of intensities associated with a 2-dimensional grid;
searching for a set of N landmarks on either an end-diastole (ED) line or an end-systole (ES) line in said image that maximizes a detection probability $$p(O|I(y_1, y_2, \ldots, y_N)) = \prod_{n=1,\ldots N} p_n^L(O|I(y_n)) \cdot p^G(O|I(y_1, y_2, \ldots, y_N)),$$

wherein $(y_1, y_2, \ldots, y_N)$ are landmark locations in said image, $I(y_1, y_2, \ldots, y_N)$ is an image patch extracted from said image using the parameter $(y_1, y_2, \ldots, y_N)$, $p(O|I(y_1, y_2, \ldots, y_N))$ is a probability of being a target landmark, $I(y_n)$ is a local image patch defined by landmark $y_n$, $p_n^L(O|I(y_n))$ is a local classifier for landmark $y_n$, and $p^G(O|I(y_1, y_2, \ldots, y_N))$ is a global detection probability of detecting said N landmarks simultaneously, wherein said landmarks are used for measuring ventricular dimensions.

9. The method of claim 8, wherein running the local detectors reduces an N-dimensional parameter space defined by said landmarks into a union of subsets containing possible landmark detections detected by said local classifiers by filtering those that fail to be detected by the local detector, wherein each dimension of said parameter space corresponds to one of the set of landmarks, and further comprising:
for each combination of possible landmarks, checking if an order of the possible landmarks is consistent with a known ordering of said landmarks; and
running said global detector on each consistent combination of possible landmarks to find a possible landmark combination with a highest detection probability as a confirmed landmark detection.

10. A non-transitory program storage device readable by a computer, tangibly embodying a program of instructions executable by the computer to perform the method steps for measuring ventricular dimensions from M-mode echocardiograms, said method comprising the steps of:
providing a digitized M-mode echocardiogram image comprising a plurality of intensities associated with a 2-dimensional grid;
running a plurality of local classifiers, wherein each local classifier trained to detect a landmark on either an end-diastole (ED) line or an end-systole (ES) line in said image, and recording all possible landmarks detected by said classifiers, wherein a search range in an N-dimensional parameter space defined by said landmarks for each dimension is reduced into a union of subsets containing said possible landmark detection, wherein each dimension of said parameter space corresponds to one of the plurality of landmarks;
for each combination of possible landmarks, checking if an order of the possible landmarks is consistent with a known ordering of said landmarks; and
if said order is consistent, running a global detector on each consistent combination of possible landmarks to find a possible landmark combination with a highest detection probability as a confirmed landmark detection, wherein said landmarks are used for measuring ventricular dimensions.

11. The computer readable program storage device of claim 10, wherein there are 5 landmarks on the ED line and 4 landmarks on the ES line.

12. The computer readable program storage device of claim 10, the method further comprising:
smoothing a landmark probability response line output by a local classifier to find all local maxima;
ranking the local maxima based on their response magnitudes; and
for each local maxima, if a minimum distance of a local maximum with respect to another local maximum in a mode point set is greater than a pre-determined threshold, then said local maximum is added to the mode point set, wherein said mode point set forms a combination of possible landmarks, and wherein said mode point set is initialized to local maximum having a highest response from said local classifiers.

13. The computer readable program storage device of claim 10, the method further comprising:
warping locations $\{y_1, \ldots, y_N\}$ of said possible landmarks along a line to coincide with canonical locations $\{z_1, \ldots, z_N\}$ of known landmarks by solving for a function $$f(z) = \sum_{n=1,\ldots,N} c_n \phi(|z-z_n|) + z \cdot d,$$

where $\phi(r)=r^2 \log(r)$ and $\{c_1, c_2, \ldots, c_N, d\}$ are coefficients, wherein $y_n = f(z_n)$.

14. The computer readable program storage device of claim 13, wherein the coefficients $\{c_1, c_2, \ldots, c_N, d\}$ are determined by solving $$\begin{bmatrix} y_1 \\ y_2 \\ \vdots \\ y_N \\ d \end{bmatrix} = \begin{bmatrix} 0 & \phi(|z_1-z_2|) & \ldots & \phi(|z_1-z_N|) & z_1 \\ \phi(|z_2-z_1|) & 0 & \ldots & \phi(|z_2-z_N|) & z_2 \\ \vdots & \vdots & \vdots & \vdots & \vdots \\ \phi(|z_N-z_1|) & \phi(|z_N-z_2|) & \ldots & 0 & z_N \\ 0 & 0 & \ldots & 0 & 1 \end{bmatrix} \begin{bmatrix} c_1 \\ c_2 \\ \vdots \\ c_N \\ d \end{bmatrix}.$$

15. The computer readable program storage device of claim 10, wherein each of said local classifiers and said global classifier are binary decision trees trained as probabilistic boosting trees wherein each tree node is a strong classifier that combines multiple weak classifiers trained on images with pre-identified landmarks.

16. The method of claim 15, wherein said weak classifiers are modeled by Haar wavelet features that represent image features.

\* \* \* \* \*